US004001706B2

United States Statutory Invention Registration [19]

[11] Reg. Number: H1706

Mason

[45] Published: Jan. 6, 1998

[54] OSTEOTOMY GUIDE

[75] Inventor: Peter H. Mason, Belleville, Ill.

[73] Assignee: The United States of America as represented by the Secretary of the Air Force, Washington, D.C.

[21] Appl. No.: 687,067

[22] Filed: Jul. 8, 1996

[51] Int. Cl.[6] ..... A61F 5/00

[52] U.S. Cl. ..... 606/87

[58] Field of Search ..... 606/87

[56] References Cited

U.S. PATENT DOCUMENTS 4,750,481 6/1988 Reese ..... 606/87

*Primary Examiner*—Charles T. Jordan
*Assistant Examiner*—Meena Chelliah
*Attorney, Agent, or Firm*—Fredric L. Sinder; Thomas L. Kundert

[57] ABSTRACT

A new osteotomy guide for guiding saw blades when making an osteotomy cut in a bone is disclosed. Osteotomy is the surgical dividing of bone. The guide includes a base, a pair of prongs and a handle. The base includes a bore for passage of a K-wire or other guide pin. The prongs define a slot for passage of a surgical saw blade. The bore and slot are deeper than prior art osteotomy guides and thus stabilize the guide and the blade relative to the guide pin so that the plane of the saw blade remains parallel to the guide pin. This ensures that in multiple-cut osteotomy procedures all the planes of opposing cuts will exactly coincide when the cut ends are reattached.

4 Claims, 1 Drawing Sheet

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

OSTEOTOMY GUIDE

The invention described herein may be manufactured and used by or for the Government of the United States for all governmental purposes without the payment of any royalty.

BACKGROUND OF THE INVENTION

The present invention relates generally to osteotomy guides for guiding saw blades when making an osteotomy cut in a bone, and more specifically to an osteotomy guide that both guides and stabilizes the blade so that planes of opposing cuts will exactly coincide.

Osteotomy is the surgical dividing of bone. An osteotomy procedure generally involves cutting completely through a bone, often removing a section of bone, and then reattaching the cut ends in a new position relative to each other to correct many types of bone deformities and misalignments and to alleviate other conditions. An example osteotomy procedure is a bunionectomy. A bunion, an inflamed swelling usually on the inside (medial side) of the first metatarsal phalangeal joint of the big toe, can be excruciatingly painful, particularly when continuously rubbed against the inside of a patient's shoe. A patient will often compensate for the pain by changing the way he or she walks and even by giving up the wearing of shoes. In a bunionectomy, a surgeon will completely divide the bone near the bunion, slide or displace the toe end of the bone toward the outside (lateral side) of the foot and reattach the two cut ends. This moves the affected metatarsal phalangeal joint away from the inside of the patient's footware, reduces pain and aggravation and may even prevent future inflammation. Another example osteotomy procedure would be to correct bowleggedhess by cutting out and removing a wedge-shaped section of a knee and then repositioning the cut ends together so that the leg is straightened.

An osteotomy typically involves more than one cut straight through a bone. A single cut leaving two plane surfaces to be reattached is mechanically weak. To provide mechanical strength and stability to the refastened bone, several cuts are generally made so that one cut end will nest into the opposite cut end, similar to, but generally not so elaborate as, a woodworking tongue-and-groove joint. An example multiple-cut osteotomy is a V-cut. The apex of the V is usually defined by a surgical guide pin, using a K-wire, that is drilled in place after a surgeon decides where the cuts should be made.

In any osteotomy where more than two cuts are required, success requires that the planes of opposing cuts coincide with each other. This is particularly difficult when the cuts are made at an angle. If they do not coincide, then the bone will be misaligned when reattached and correction will require substantial additional cutting. Imagine, for example, the difficulty of correcting a woodworking tongue-and-groove joint if the walls of the tongue or the groove were at different angles relative to each other. A particular difficulty facing surgeons performing osteotomy procedures is that they have only a two-dimensional view for making three-dimensional cuts.

Prior art osteotomy guides which attach to a guide pin, such as the Scott Universal, the Austin/Scarf and the Austin/Chevron, do not provide stability for the osteotomy blade and do not provide a feature for modifying the angle of osteotomy cuts. The Scott RCE osteotomy guide does provide for modifying the angle of osteotomy cuts, but does not stabilize the osteotomy blade. The Scott RCE osteotomy guide is also large and bulky, necessitating excessive dissection to make room for the guide.

The result of using these prior art osteotomy guides is that a successful surgical outcome is not only too highly dependent on a surgeon's skill, but also that they require excessive tissue excision so that the surgeon can see where he or she is cutting.

Thus it is seen that there is a need for an improved osteotomy guide that helps ensure in an osteotomy procedure accurate placement of a surgical saw blade so that the planes of opposing osteotomy cuts will exactly coincide.

It is, therefore, a principal object of the present invention to provide an osteotomy guide that, in addition to guiding a surgical saw blade, also stabilizes and supports the saw blade.

It is another object of the present invention to provide an osteotomy guide that holds the saw blade parallel to the guide pin.

It is a feature of the present invention that it holds the saw blade parallel to a guide pin during cutting.

It is another feature of the present invention that it ensures precise placement of the saw blade and accurate cuts.

It is a further feature of the present invention that it is inexpensive and straightforward to make.

It is yet another feature of the present invention that it can be easily modified for any type of surgical procedure.

It is a yet further feature of the present invention that it can vary the angle of the osteotomy cut.

It is an advantage of the present invention that it reduces the amount of soft tissue dissection needed to perform an osteotomy, particularly the need for additional dissection to open the surgical area for further cutting to correct a misalignment.

It is another advantage of the present invention that it makes osteotomy procedures easier to perform and increases a surgeon's confidence.

These and other objects, features and advantages of the present invention will become apparent as the description of certain representative embodiments proceeds.

SUMMARY OF THE INVENTION

The present invention provides an osteotomy guide for guiding surgical saw blades when making an osteotomy cut in a bone. The breakthrough discovery of the present invention is that an osteotomy guide, in addition to guiding the saw blade, must also stabilize and support the blade so that the planes of opposing cuts will exactly coincide.

Accordingly, the present invention is directed to an osteotomy guide for guiding an osteotomy blade during cutting of bone, comprising a guide pin holder sized and shaped such that the guide pin holder can rotate about a guide pin while being held at a first fixed angle relative to the guide pin, and an osteotomy blade stabilizer connected to the guide pin holder such that the osteotomy blade stabilizer will be held at a fixed angle relative to the guide pin, the osteotomy blade holder sized and shaped such that the osteotomy blade can move translationally while the plane of the osteotomy blade is held at a second fixed angle relative to the guide pin. The osteotomy guide may include having the first fixed angle and the second fixed angle both 180° so that the plane of the osteotomy blade is held parallel to the guide pin.

The present invention is also directed to an osteotomy guide for guiding an osteotomy blade during cutting of bone, comprising a base defining a bore, the bore having a diameter such that it will rotatably hold a guide pin and having a depth such that the base will be held at a fixed angle relative to the guide pin, extending from the base, a pair of prongs defining a slot parallel to the bore, the slot having a width and depth such that the plane of the osteotomy blade will be held parallel to the guide pin as the osteotomy blade moves up and down through the slot, and a handle connected to the base.

The present invention is further directed to an osteotomy guide for guiding an osteotomy blade during cutting of bone, comprising a base defining a bore, the bore having a diameter such that it will rotatably hold a guide pin and having a depth such that the base will be held at a fixed angle relative to the guide pin, extending horizontally from the base, a pair of prongs defining a slot at a fixed angle relative to the bore, the slot having a width and depth such that the plane of the osteotomy blade will be held at a fixed angle relative to the guide pin as the osteotomy blade moves up and down through the slot, and a handle connected to the base.

BRIEF DESCRIPTION OF THE DRAWINGS

The present invention will be more clearly understood from a reading of the following detailed description in conjunction with the accompanying drawings wherein.

DETAILED DESCRIPTION

Figure 1:
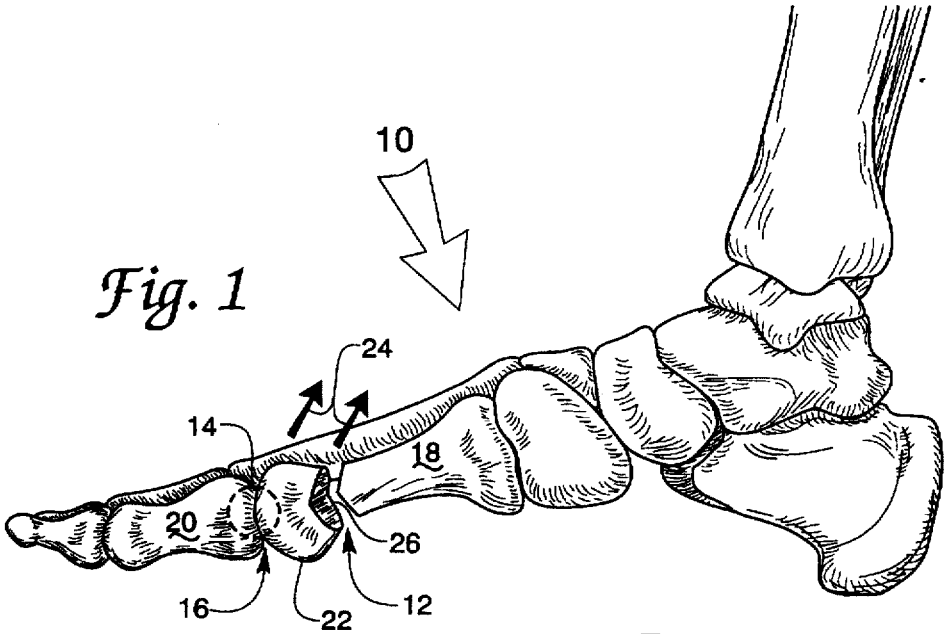
FIG. 1 is a simplified perspective view of the bones of a foot showing an exploded view of a typical bunionectomy osteotomy cut.

Referring now to FIG. 1 of the drawings, there is shown a simplified perspective view of the bones of a foot 10 including an exploded view of a typical bunionectomy osteotomy cut 12. As described in the Background of the Invention, a bunion, indicated by dashed outline 14, will typically be located at the joint 16 between the first metatarsal bone 18 and the proximal phalange bone 20 of the big toe. By making cut 12 as shown and then laterally (toward the outside of foot 10) displacing the metatarsal head 22 relative to the rest of metatarsal 18, as indicated by arrows 24, affected metatarsal phalangeal joint 16 is moved away from where it will contact a patient's footware.

Osteotomy cut 12 is V-shaped so that, as described in the Background of the Invention, when reattached the shape of the cut will provide some structural support. Moreover, V-shaped cut 12 must be properly aligned relative to metatarsal head 22 or the surgery will cause further problems. For example, if the apex, or axis, 26 of cut 12 is too far forward (distal) there is a risk of nonunion when the cut ends are reattached. If axis 26 of cut 12 is too far back (proximal), then a metatarsal head fracture or a vascular necrosis may result. Similarly, if axis 26 is not straight through metatarsal head 22, but is tilted medially or laterally (up or down) then, when reattached, metatarsal head 22 may point in a different direction or metatarsal 18 may be longer or shorter than normal (beyond the shortening that results from lost bone tissue from the cutting itself). An equally serious problem is that if the planes of opposing cuts are not perfectly aligned relative to each other, the cut ends will not align and more bone tissue will be lost in correcting the misalignment.

During surgery, axis 26 is defined by a guide pin, usually a so-called K-wire, that is drilled into metatarsal head 22. Osteotomy guides attach to the guide pin or K-wire to guide the saw blade of a hand-held saggital saw to make the cuts.

The problems revealed by the exemplary bunionectomy are common to all osteotomy procedures.

Figure 2:
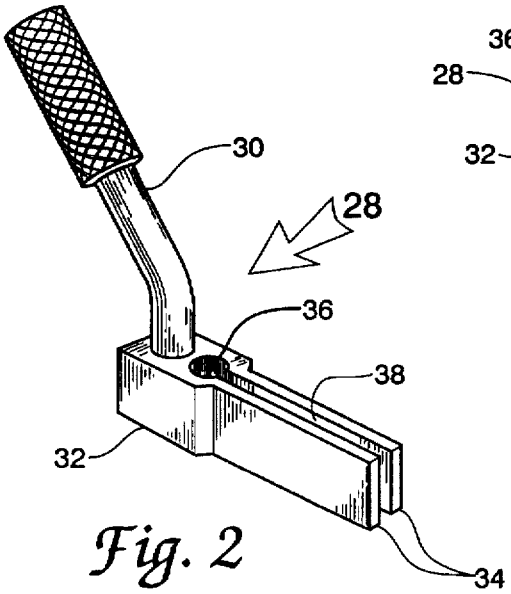
FIG. 2 is a perspective view of an osteotomy guide made according to the teachings of the present invention; and, FIG. 3 is a perspective view of the osteotomy guide of FIG. 1 being used to perform an bunionectomy on a foot, the soft tissue surrounding the bones not being shown to make the drawing easier to view.

FIG. 2 is a perspective view of an osteotomy guide 28 made according to the teachings of the present invention. Osteotomy guide 28 comprises a handle 30, a base 32 and a pair of prongs 34. Base 32 has a bore 36 for passage of a K-wire or other guide pin or axis guide. Prongs 34 define a slot 38 for passage of a surgical saw blade. Bore 36 has a diameter such that a guide pin will just fit inside bore 36 and a depth such that osteotomy guide 28 will not twist or rock about the guide pin. Prongs 34 are of sufficient width and separation, and slot 38 resultingly of sufficient depth and width, so that a saw blade will be stabilized and supported as it moves up and down through slot 38. Together, the dimensions of bore 36 and slot 38 ensure that a saw blade will be held at a fixed angle, preferably parallel, to the guide pin.

Figure 3:
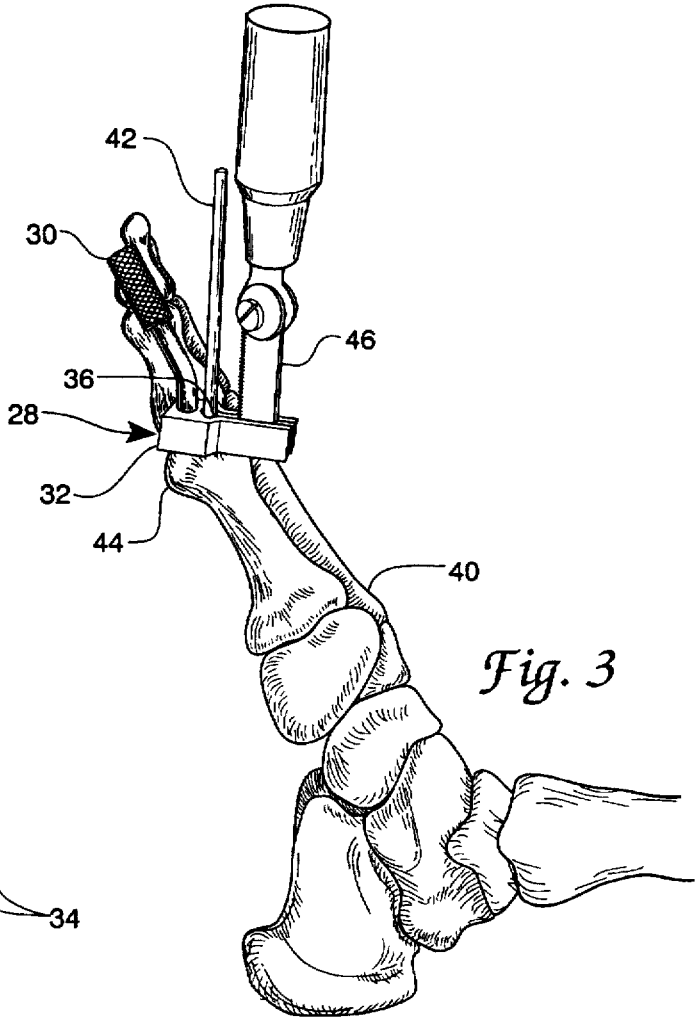

FIG. 3 is a perspective view of osteotomy guide 28 being used to perform an bunionectomy on a foot 40 (the soft tissue surrounding the bones of foot 40 are not shown to make the drawing easier to view). After a K-wire 42 is drilled into a metatarsal head 44, osteotomy guide 28 is placed around K-wire 42 so that K-wire 42 is rotatably secured inside bore 36 and the path for each cut determined by the surgeon. The surgeon then holds osteotomy guide 28 by handle 30, and with slot 38 securely holding a saw blade 46 in line with K-wire 42, makes each cut. Any deviation of saw blade 46 from the path determined by the surgeon will create an inaccurate and unstable osteotomy. By the use of osteotomy guide 28, the planes of each cut will intersect with K-wire 42 and the intended apex of the V-cut. This ensures a perfect "V" without the cuts converging or diverging as they proceed laterally. All four osteotomy surfaces will then exactly coincide when the cut ends are reattached.

The angle of the "V" should be 60° for greatest stability. That is why most prior art osteotomy guides are fixed at 60°. Some procedures, however, require a longer top (dorsal) arm osteotomy cut, such as for attachment screw placement. With osteotomy guide 28, this can be accomplished while making certain that the saw blade remains parallel with the K-wire for both cuts.

The preferred dimensions for an osteotomy guide sized for a conventional bunionectomy include prong lengths of 2 cm, a guide pin bore diameter sized for a 0.062 inch K-wire, and a handle 4 cm high. Persons of ordinary skill in the art will find it routine to resize the osteotomy guide for other osteotomy procedures.

The disclosed osteotomy guide successfully demonstrates the advantages of adding a saw blade stabilizing feature to the guiding function of prior art osteotomy guides. The disclosed guide can be used to facilitate any surgical procedure where control of a saw blade or other cutting device and convergence of multiple cuts are required. Although the disclosed guide is specialized, its teachings will find application in other areas where intricate procedures are performed by hand.

Those with skill in the field of the invention will readily see modifications that can be made to the invention as described, yet still within the intended scope of the claims. Therefore, all embodiments contemplated have not been shown in complete detail. Other embodiments may be developed without departing from the spirit of the invention or from the scope of the claims.

I claim:

1. An osteotomy guide for guiding an osteotomy blade during cutting of bone, comprising:

(a) a guide pin holder sized and shaped such that the guide pin holder can rotate about a guide pin while being held at a first fixed angle relative to the guide pin; and, (b) an osteotomy blade stabilizer connected to the guide pin holder such that the osteotomy blade stabilizer will be held at a fixed angle relative to the guide pin, the osteotomy blade holder sized and shaped such that the osteotomy blade can move translationally while the plane of the osteotomy blade is held at a second fixed angle relative to the guide pin.

2. The osteotomy guide according to claim 1, wherein the first fixed angle and the second fixed angle are both 180° so that the plane of the osteotomy blade is held parallel to the guide pin.

3. An osteotomy guide for guiding an osteotomy blade during cutting of bone, comprising:

(a) a base defining a bore, the bore having a diameter such that it will rotatably hold a guide pin and having a depth such that the base will be held at a fixed angle relative to the guide pin;

(b) extending from the base, a pair of prongs defining a slot parallel to the bore, the slot having a width and depth such that the plane of the osteotomy blade will be held parallel to the guide pin as the osteotomy blade moves up and down through the slot; and, (c) a handle connected to the base.

4. An osteotomy guide for guiding an osteotomy blade during cutting of bone, comprising:

(a) a base defining a bore, the bore having a diameter such that it will rotatably hold a guide pin and having a depth such that the base will be held at a fixed angle relative to the guide pin;

(b) extending horizontally from the base, a pair of prongs defining a slot at a fixed angle relative to the bore, the slot having a width and depth such that the plane of the osteotomy blade will be held at a fixed angle relative to the guide pin as the osteotomy blade moves up and down through the slot; and, (c) a handle connected to the base.

* * * * *